United States Patent [19]

Rodgers et al.

[11] Patent Number: 5,124,467

[45] Date of Patent: Jun. 23, 1992

[54] PERFLUOROALKYPOLYOXYALKYL-POLYSILOXANE SURFACTANTS

[75] Inventors: Juliana Rodgers, Staten Island; Athanasios Karydas, New York, both of N.Y.

[73] Assignee: Ciba-Geigy Corporation, Ardsley, N.Y.

[21] Appl. No.: 556,068

[22] Filed: Jul. 20, 1990

[51] Int. Cl.$^5$ .............................. C07F 7/08; C07F 7/10
[52] U.S. Cl. ................................... 556/427; 556/413; 556/419; 556/422; 556/428; 556/436; 556/437; 556/448
[58] Field of Search ............... 556/448, 427, 413, 437, 556/428, 436, 419, 422

[56] References Cited

U.S. PATENT DOCUMENTS

| | | | |
|---|---|---|---|
| 3,132,117 | 5/1964 | Schmidt | 556/448 X |
| 3,529,003 | 9/1970 | Rausch et al. | 556/448 |
| 3,772,346 | 11/1973 | Hess | 556/448 X |
| 3,809,783 | 5/1974 | Pittman et al. | 556/448 X |
| 4,927,950 | 5/1990 | Hisamoto et al. | 556/419 |
| 4,968,828 | 11/1990 | Yamamoto | 556/448 |

OTHER PUBLICATIONS

Dow Corning Brochure "Information about Cosmetic Ingredients", (1980).
Union Carbide "Silwet Surfactants" (Feb. 1988).

*Primary Examiner*—Paul F. Shaver
*Attorney, Agent, or Firm*—Kevin T. Mansfield; Edward McC. Roberts

[57] ABSTRACT

The instant invention relates to polysiloxane polyoxyalkylene compounds containing at least one perfluoroalkyl terminated polyoxyalkylene group. These compounds are useful as surfactants and improve or impart properties such as wetting, penetration, spreading, levelling, foam stability, flow properties, dispersion properties and oil and water repellency.

11 Claims, No Drawings

PERFLUOROALKYPOLYOXYALKYL-POLYSILOXANE SURFACTANTS

BACKGROUND OF THE INVENTION

Block copolymers containing polysiloxane segments and polyoxyalkylene segments are widely used as surface active agents in coatings, urethane foams, plastics, textiles and printing processes, to name only a few applications. Specifically, the silicone compounds are composed of a siloxane backbone with polyalkylene oxide pendants. Members of this class, when dissolved in water, achieve low surface tension values (as low as 20 dynes/cm.), an ability only exceeded by fluorocarbon surfactants.

Fluorochemical surfactant compounds are the most effective surface active agents known, reducing the surface tension of water to as low as 15 dynes/cm. The unique surface activity of fluorosurfactants is attributed to the ability of the perfluoroalkyl groups to pack at the air-water interface.

Fluorochemical surfactants, however, are quite costly at $20-50/lb compared to the silicone surfactants which are available at about $5/lb. For this reason, fluorosurfactants are prohibitively used in applications that require surface active agents.

In this invention, we have developed a new class of surfactants containing both silicone and perfluoroalkyl groups. We have shown improvement in surface active properties of alkoxylated siloxanes by modification of the alkylene oxide pendants with perfluoroalkyl containing groups. These novel perfluoroalkyl modified silicones exhibit greater surface activity i.e. lower surface tension, than the parent siloxane, even at 10% of the concentration. As a result, they improve or impart properties such as wetting, penetration, spreading, levelling, foam stability, flow properties, dispersion properties and oil and water repellency. Their cost is competitive with the silicone surfactants since only a small amount of a perfluoroalkyl moiety is required to improve surface properties and since the use level required to obtain similar performance is greatly reduced.

DETAILED DESCRIPTION OF THE INVENTION

The present invention relates to polysiloxane polyoxyalkylene compounds containing at least one perfluoroalkyl terminated polyoxyalkylene group, represented by the general formula

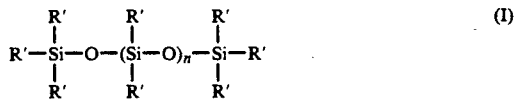

wherein n is 1 to 200,

R' is independently branched or straight chain alkyl of up to 18 carbon atoms, aryl of up to 10 carbon atoms, aralkylene of up to 14 carbon atoms or

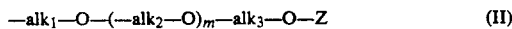

with the proviso that at least one R' is of the formula

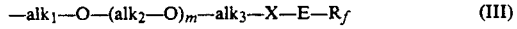

where $alk_1$ is independently alkylene of up to 20 carbon atoms, $alk_2$ and $alk_3$ are alkylene of up to 4 carbon atoms, or said alkylene substituted by hydroxy, $-COO^-A^+$, $-SO_3^-A^+$, $-N^+(R)_3B^-$, or $-OSO_3^-A^+$, or by alkoxy of up to 15 carbon atoms or by said alkoxy interrupted by one to three groups independently selected from the group consisting of $-NR-$, $-N^+(R)_2^-$, $-O-$, $-SO_2-$, $-COO-$, $-OOC-$, $-CONR-$, $-NRCO-$, $-SO_2NR-$, $-NRSO_2-$ or $-CO-$, or wherein said alkoxy or interrupted alkoxy is substituted by hydroxy or by $-CO_2^-A^+$, $SO_3^-A^+$, $-N^+(R)_3B^-$ or $-OSO_3^-A^+$ or mixtures thereof; Z is hydrogen or straight or branched chain alkyl of up to 15 carbon atoms or said alkyl interrupted by one to three groups independently selected from the group consisting of $-NR-$, $-N^+(R)_2^-$, $-O-$, $-S-$, $-SO_2-$, $-COO-$, $-OOC-$, $-CONR-$, $-NRCO-$, $-SO_2NR-$, $-NRSO_2-$, or $-CO-$; or Z is said alkyl or interrupted alkyl substituted by hydroxy or by $-CO_2^-A^+$, $-SO_3^-A^+$, $-N^+(R)_3B^-$, $-OSO_3^-A^+$ where A in each case is a positively charged counterion such as hydrogen, an alkali or alkaline earth metal or $N(R)_4^+$, and where B is a counteranion such as halo, hydroxy, lower alkanoyloxy, or lower alkylsulfonate; R is independently hydrogen, alkyl of 1 to 6 carbon atoms, or hydroxyalkyl of 1 to 6 carbon atoms; m is 0 to 100; E is straight or branched chain alkylene or hydroxy substituted alkylene of up to 15 carbon atoms or said alkylene or hydroxy substituted alkylene interrupted by one to three groups independently selected from the group consisting of $-NR-$, $-O-$, $-S-$, $-SO_2-$, $-COO-$, $-OOC-$, $-CONR-$, $-NRCO-$, $-SO_2NR-$, and $-NRSO_2-$, or terminated at the $R_f$ end with $-CONR-$ or $-SO_2NR-$ where $R_f$ is attached to the respective carbonyl carbon or sulfur atom thereof, and X is $-S-$, $-O-$, $-SO_2-$, $-NR-$, $-NRSO_2-$, $-SO_2NR-$, $-NRCO-$, $-CONR-$, $-CR_2-$, $-OOC-$; or E is a direct bond and X is $-CONR-$ or $-SO_2NR-$ where $R_f$ is attached to the respective carbonyl carbon or sulfur atom thereof; R is defined as above; and $R_f$ is independently a straight or branched chain perfluoroalkyl of up to 18 carbon atoms or said perfluoroalkyl substituted by perfluoroalkoxy of 2 to 6 carbon atoms, or mixtures thereof.

Where R' is alkyl, it is preferably alkyl of up to 4 carbon atoms, most preferably methyl; n is preferably 1 to 100; $alk_1$ is preferably alkylene of 3 to 10 carbon atoms; $alk_2$ and $alk_3$ are preferably alkylene of 2 to 4 carbon atoms, or mixtures thereof, Z is hydrogen or lower alkyl, m is preferably 1 to 50, most preferably 4 to 50; E is preferably alkylene of up to 3 carbon atoms, $-CH_2CH_2S(C_3H_5OH)-$, $-CH_2CH_2SO_2(C_3H_5OH)-$ or $-SO_2N(C_2H_5)CH_2CH_2S(CH_2)_3O(C_3H_5OH)-$, and X is $-O-$; $R_f$ is perfluoroalkyl of 4 to 12 carbon atoms or perfluoroalkyl of 2 to 6 carbon atoms substituted by perfluoroalkoxy of 2 to 6 carbon atoms, or mixtures thereof. The groups $C_3H_5OH$ advantageously refers to hydroxy substituted alkylene of 3 carbon atoms, preferably $-CH_2CH(OH)CH_2-$, $-CH(CH_2OH)CH_2-$ or $-CH_2CH(CH_2OH)-$.

A preferred subgenus relates to those compounds of formula I containing at least one perfluoroalkyl terminated polyoxyalkylene group of the formula

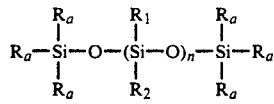

wherein $R_a$ is independently branched or straight chain alkyl of up to 18 carbon atoms, aryl of up to 10 carbon atoms or aralkylene of up to 14 carbon atoms; n is 1 to 200; at least one of $R_1$ and $R_2$ is

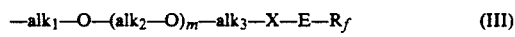

and the remainder of $R_1$ and $R_2$ are independently branched or straight chain alkyl of up to 18 carbon atoms, aryl of up to 10 carbon atoms, aralkylene of up to 14 carbon atoms or

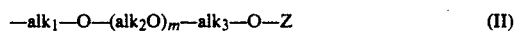

wherein $alk_1$, $alk_2$, $alk_3$, X, E, $R_f$, m and Z are as defined above.

Preferred compounds of formula Ia are those where $R_a$ is independently alkyl of 1 to 4 carbon atoms, most preferably methyl; n is independently an integer preferably 1 to 100; at least one of $R_1$ or $R_2$ is given according to formula III, and the remainder of $R_1$ and $R_2$ are independently and preferably branched or straight chain alkyl of 1 to 4 carbon atoms, most preferably methyl, or given by formula II.

Most preferred for formulae II and III are where $alk_1$ is independently alkylene of 3 to 10 carbon atoms; $alk_2$ and $alk_3$ are independently alkylene of 2 to 4 carbon atoms, or mixtures thereof; Z is hydrogen or lower alkyl, most preferably hydrogen or methyl; m is independently an integer from 1 to 50; E is alkylene of 1 to 3 carbon atoms, —CH$_2$CH$_2$S(C$_3$H$_5$OH)—, —CH$_2$CH$_2$SO$_2$(C$_3$H$_5$OH)—, —SO$_2$N(C$_2$H$_5$)CH$_2$CH$_2$S(CH$_2$)$_3$O(C$_3$H$_5$OH)—, and X is —O—; $R_f$ is perfluoroalkyl of 4 to 12 carbon atoms or perfluoroalkyl of 2 to 6 carbon atoms substituted by perfluoroalkoxy of 2 to 6 carbon atoms, or mixtures thereof.

It is understood that the $R_f$ group in formula III preferably represents a mixture of perfluoroalkyl moieties. When the $R_f$ group is identified as having a certain number of carbon atoms, said $R_f$ group also usually concomitantly contains a small fraction of perfluoroalkyl groups with a lower number of carbon atoms and a small fraction of perfluoroalkyl groups with a higher number of carbon atoms.

The compounds of formula I and Ia may be prepared by methods generally known to the art.

For example, the compounds of formula I and Ia where X is —O— in formula III may be prepared from a corresponding polysiloxane-polyoxyalkylene copolymer of the formula

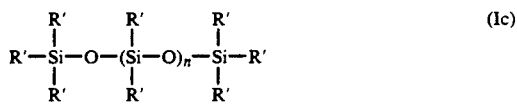

wherein n is 1 to 200, R' is independently branched or straight chain alkyl of up to 18 carbon atoms, aryl of up to 10 carbon atoms, aralkylene of up to 14 carbon atoms or —alk$_1$—O—(—alk$_2$—O)$_m$—alk$_3$—O—Z with the proviso that at least one R' is —alk$_1$—O—(alk$_2$—O)$_m$—alk$_3$—OH where the groups are otherwise as defined above, or of the formula

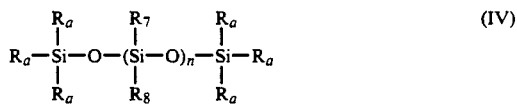

where $R_a$ is defined as above, at least one of $R_7$ and $R_8$ is defined by formula II with at least one Z being hydrogen and the remainder of $R_7$ and $R_8$ are independently branched or straight chain alkyl of up to 18 carbon atoms, aryl of up to 10 carbon atoms or aralkylene of up to 14 carbon atoms, by reacting said alkoxylated siloxane of formula Ic or IV, respectively, with a fluorinated epoxide of the formula

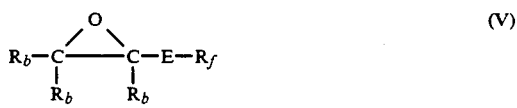

where $R_b$ is hydrogen or lower alkyl, preferably hydrogen; and E and $R_f$ are as defined above. The syntheses of fluorinated epoxides of the formula V are described in U.S. Pat. No. 4,577,036. Typical epoxides which can be used within the context of this invention are:

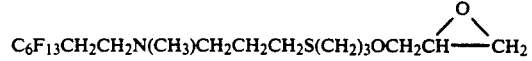

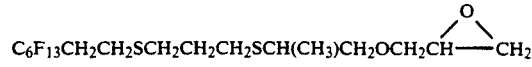

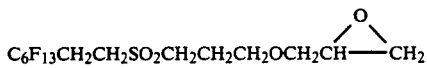

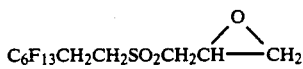

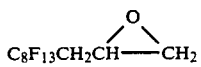

The compounds of formula Ic and IV are as a class old in the art, and may be prepared by conventional techniques.

The epoxide is used in an equimolar amount or less than an equimolar amount relative to the hydroxy group terminating the polyoxyalkylene group. The addition of the epoxide to the hydroxy group is carried out in the presence of a lewis acid catalyst such as aluminum chloride or boron trifluoride (usually in the form of the diethyl ether complex thereof), or a base such as benzyl trimethyl ammonium hydroxide, at a temperature between 30° C. and 120° C. Use of a solvent is optional. Suitable inert solvents include ketones such as acetone or methyl ethyl ketone; ethers such as diethyl ether, ethyleneglycol-dimethylether or tetrahydrofuran; esters such as ethyl acetate; aromatic hydrocarbons such as toluene; and amides such as dimethylformamide or N-methyl pyrolidone. Where convenient, it is preferred to carry out the addition reaction in bulk i.e. in the absence of solvent.

Also, those compounds of formula I and Ia, containing X as —S— in formula III may be prepared by first converting the hydroxy group or groups of a polysiloxane-polyoxyalkylene copolymer of formula Ic or IV, respectively, to a halide group, preferably bromide using phosphorus oxybromide. The bromide is then displaced with a terminal perfluoroalkyl containing mercaptan such as R$_f$CH$_2$CH$_2$SH in the presence of an equimolar amount of potassium carbonate. Such reactions are conveniently conducted between 30° C. and 120° C. in an inert solvent or diluent such as toluene, dimethylformamide, perchloroethylene, preferably lower alkanones as acetone or methyl ethyl ketone. By-product salts are removed by filtration; solvent is optionally removed by vacuum distillation.

In addition, the resulting thio-linkage can be oxidized by conventional oxidizing agents as meta-chloroperbenzoic acid or peracetic acid, to produce the corresponding sulfone linkage as X in formula III of formula I and Ia, respectively. The reaction is carried out in an inert solvent such as a halogenated hydrocarbon, e.g. chloroform, or the like, at a reaction temperature between 10° C. to about 50° C. Elevated temperatures and an excess of peroxide favor the formation of the sulfone.

Alternatively, those compounds of formula I and Ia where X is —NHSO$_2$— in formula III, can be prepared by first converting the hydroxy group or groups of a polysiloxane-polyoxyalkylene copolymer of formula Ic or IV, respectively, to a halide, preferably bromide, as described above, and then reacting the halide intermediate with ammonia followed by caustic to give the corresponding amine. The amine intermediate can then be reacted with a terminal perfluoroalkyl containing sulfonyl chloride as C$_8$F$_{17}$SO$_2$Cl producing the sulfoneamido linkage.

Additionally, compounds of formula I and Ia where X of formula III is an ester linkage (—OOC—) are easily obtained by reacting the hydroxy group or groups of formula Ic or IV with an acyl chloride such as C$_7$F$_{15}$COCl, C$_8$F$_{17}$SO$_2$N(CH$_2$CH$_3$)CH$_2$COCl, C$_8$F$_{17}$CH$_2$CH$_2$SCH$_2$CH$_2$COCl, or (C$_8$F$_{17}$CH$_2$CH$_2$S)$_2$C(CH$_3$)CH$_2$CH$_2$COCl in the presence of a base such as N,N-dimethylaniline, triethylamine, or pyridine to neutralize the hydrogen halide formed. The acyl halides are readily available from the corresponding carboxylic acids according to known methods using thionyl chloride or phosphorus trichloride.

When formula I contains a hydroxy group or groups, nonionic, anionic, cationic and amphoteric derivatives of formula I can be prepared according to methods known in the art. For example, the hydroxy group or groups can be reacted with chlorosulfonic acid to yield —OSO$_3$H as the terminal group, or reacted with

in the presence of a base to produce the —O—CH$_2$CH(OH)CH$_2$N(CH$_3$)$_3$+Cl$^-$ group. Alternatively, the reaction between the hydroxy group or groups and butyrolactone yields a terminal —O—(CH$_2$)$_3$CO$_2$H group. This can further be neutralized with lithium hydroxide to produce the —O(CH$_2$)$_3$CO$_2$−Li$^+$ group, rendering the compound of formula I anionic. Additionally, the hydroxy group or groups are easily converted to the chloride using phosphorus oxychloride, which is then further reacted with N,N-dimethylglycine to produce the amphoteric moiety, —N+(CH2)2CH2CO2−.

The compounds of formula I and salts thereof are useful in rendering cellulosic and natural and synthetic polyamide materials hydrophobic and oleophobic. The compounds of the instant invention are applied to the substrate in the form of an aqueous solution or emulsion, or if substantially insoluble in water, then dissolved in an organic or aqueous/organic solvent, e.g. methanol, ethanol/water, dichloroethane and the like, and applied to the material by padding, washing or coating the surface thereof. Upon drying, the surface exhibits desirable oil and water repellent properties. Where the compounds of the instant invention are water soluble, per se, then they are useful in reducing the surface tension thereof, and the resultant solutions are useful in cleaning etc. Also, because of their surface tension lowering effects, the instant compounds find use as leveling agents for floor waxes and the like.

EXAMPLE 1

Approximately 2.5 g (0.0052 moles) of

and 20.98 g (0.0312 moles) of polyoxyalkylene-methylpolysiloxane copolymer DOW CORNING DC-193:

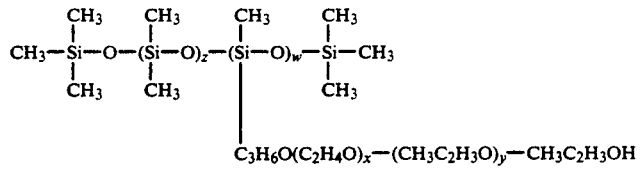

$z \approx 5\text{-}10 \quad x \approx 11\text{-}15$
$w \approx 3\text{-}5 \quad y \approx 2\text{-}4$ are combined. To this is added 0.04 g (0.0004 moles) boron trifluoride etherate. The entire mix is heated at 80°–83° C. for 4 hours under a nitrogen blanket, yielding the liquid product which contains:

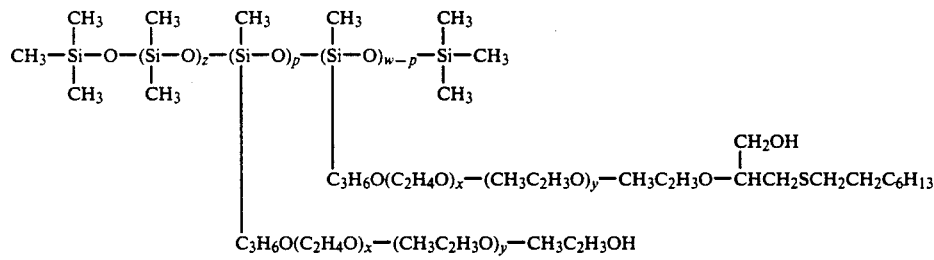

and its addition isomers

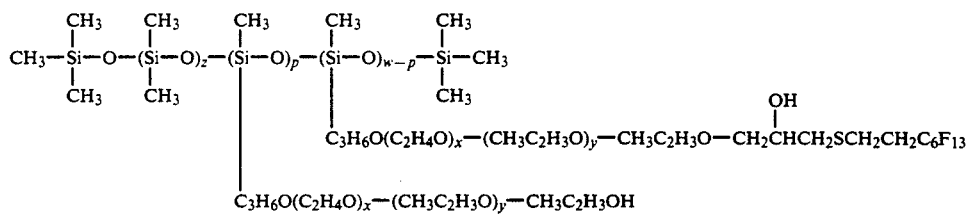

and

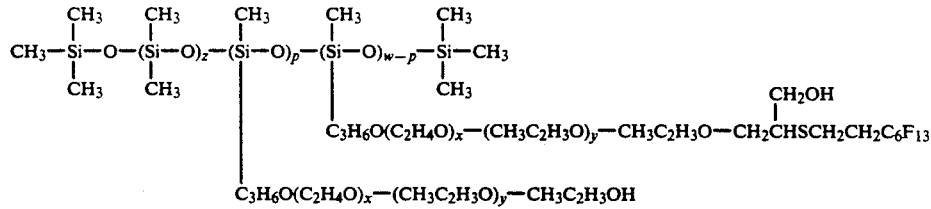

where z, w, x, y are as defined above. The molar ratio of p:w-p is 5:1, where units of p and w-p are random.

EXAMPLE 2

To a solution of 8.0 g (0.0166 moles) of

and 20.14 g (0.0300 moles) of a polyoxyalkylene-methylpolysiloxane copolymer DOW CORNING DC- 193 is added 0.04 g (0.0003 moles) boron trifluoride etherate. The reaction mixture is stirred and heated at 83° C. for 4.5 hours under a blanket of nitrogen. A clear liquid product is obtained containing:

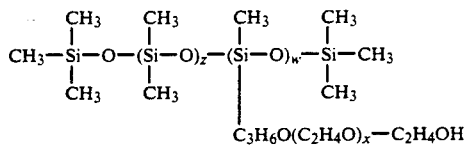

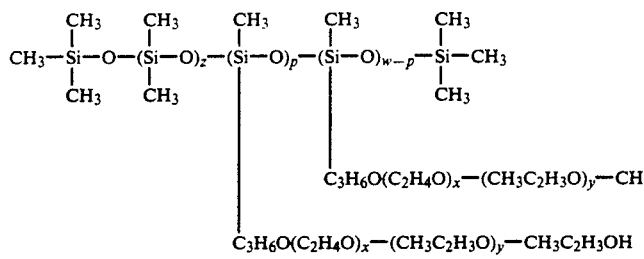

$z \approx 15\text{-}20$
$w \approx 3\text{-}5$
$x \approx 15\text{-}20$ and its addition isomers:

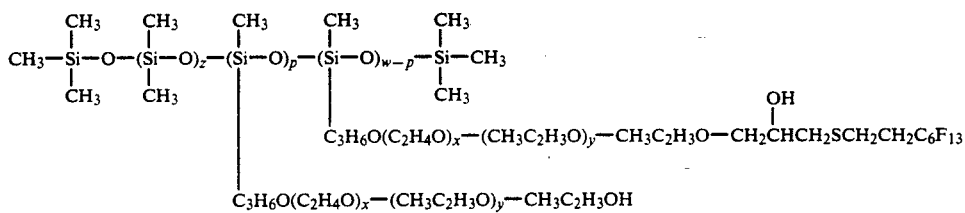

and

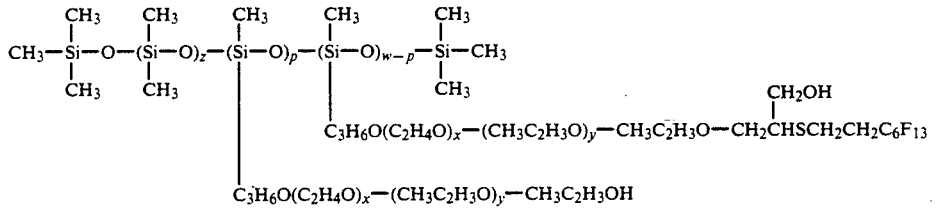

where z, w, x, y are as defined in Example 1, the molar ratio of p:w-p is 0.8:1, and where units of w-p and p are random.

EXAMPLE 3

To a flask is added 6.01 g (0.0125 moles) of

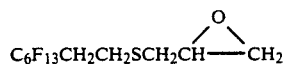

and 15.00 g (0.0125 moles) polyoxyethylene-methyl-polysiloxane copolymer SILWET L-7614 from UNION CARBIDE:

followed by 0.04 g (0.0003 moles) boron trifluoride etherate. After heating under nitrogen at 80° C. for 4.1 hours, a liquid product is obtained containing

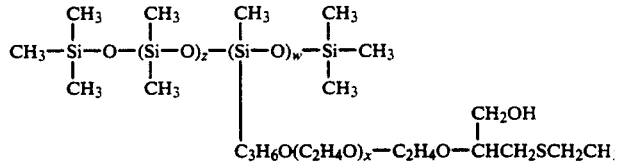

and its addition isomers:

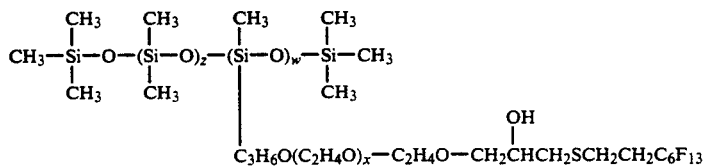

and

-continued

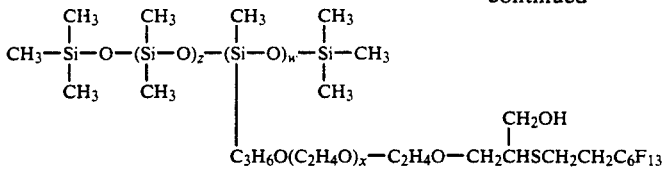

where z, w, x are as defined above.

EXAMPLE 4

| Comparative Surfactant Properties in Distilled Water | | | | | | | | |
|---|---|---|---|---|---|---|---|---|
| | Equilibrium Surface Tension[1] (dynes/cm) | | | Dynamic Surface Tension[2] at 0.1% (dynes/cm) | | | Draves Wetting[3] at 0.1% (sec) | Ross-Miles[4] at 0.1% (mm) |
| | % F | 0.1% | 0.01% | 0.001% | 1 sec | 5 sec | 10 sec | | |
| DC-193 | — | 27.9 | 29.4 | 41.5 | 54.8 | 43.5 | 38.2 | >300 | 40/30 |
| Example 1 | 5.5 | 24.4 | 27.4 | 40.2 | 47.2 | 39.5 | 36.2 | >300 | 33/13 |
| Example 2 | 14.6 | 22.7 | 25.6 | 45.0 | 43.0 | 36.8 | 33.3 | 154 | 20/10 |
| Silwet L-7614 | — | 29.3 | 31.4 | 47.8 | 50.0 | 42.0 | 38.5 | >300 | 60/45 |
| Example 3 | 14.7 | 19.7 | 23.1 | 38.9 | 44.8 | 31.8 | 28.0 | 61 | 28/25 |

[1]Wilhemy plate technique, Kruss K-10 tensiometer.
[2]Drop-Weight Technique, Jho. C. and Burke R., "J. of Colloid and Interface Science," 95, 61 (1983).
[3]ASTM method D-2281-68, sinking time in seconds.
[4]ASTM method D-1173-53 at 49° C.; initial foam height in mm and after 5 minutes.

Comparison of the above surfactant properties indicates a significant activity enhancement when the alkoxylated siloxanes are modified with fluorine. The surface activity and wetting characteristics improve even further as the fluorine content is increased.

What is claimed is:

1. A polysiloxane polyoxyalkylene compound containing at least one perfluoroalkyl terminated polyoxyalkylene group, represented by the general formula

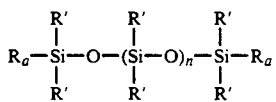

wherein
n is 1 to 200,
$R_a$ is independently branched or straight chain alkyl of up to 18 carbon atoms, aryl of up to 10 carbon atoms, or aralkylene of up to 14 carbon atoms;
R' is independently branched or straight chain alkyl of up to 18 carbon atoms, aryl of up to 10 carbon atoms, aralkylene of up to 14 carbon atoms or

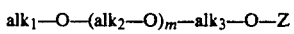

with the proviso that at least one R' is of the formula

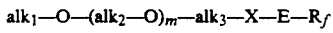

where $alk_1$ is independently alkylene of up to 20 carbon atoms, $alk_2$ and $alk_3$ are alkylene of up to 4 carbon atoms, or said alkylene substituted by hydroxy, —COO—A+, —SO$_3$—A+, —N+(R)$_3$B−, or —OSO$_3$−A+, or by alkoxy of up to 15 carbon atoms or by said alkoxy interrupted by one to three groups independently selected from the group consisting of —NR—, —N+(R)$_2$—, —O—, —S—, —SO$_2$—, —COO—, —OOC—, —CONR—, —NRCO—, —SO$_2$NR—, —NRSO$_2$— or —CO—, or wherein said alkoxy or interrupted alkoxy is substituted by hydroxy or by —CO$_2$−A+, —SO$_3$−A+, —N+(R)$_3$B− or —OSO$_3$−A+ or mixtures thereof; Z is hydrogen or straight or branched chain alkyl of up to 15 carbon atoms or said alkyl interrupted by one to three groups independently selected from the group consisting of —NR—, —N+(R)$_2$—, —O—, —S—, —SO$_2$—, —COO—, —OOC—, —CONR—, —NRCO—, —SO$_2$NR—, —NRSO$_2$—, or —CO—; or Z is said alkyl or interrupted alkyl substituted by hydroxy or by —CO$_2$−A+, —SO$_3$−A+, —N+(R)$_3$B− or —OSO$_3$−A+ where A in each case is a positively charged counterion, and where B is a counteranion; R is independently hydrogen, alkyl of 1 to 6 carbon atoms, or hydroxyalkyl of 1 to 6 carbon atoms; m is 1 to 50; E is straight or branched chain alkylene or hydroxy substituted alkylene of up to 15 carbon atoms or said alkylene or hydroxy substituted alkylene interrupted by one to three groups independently selected from the group consisting of —NR—, —O—, —S—, —SO$_2$—, —COO—, —OOC—, —CONR—, —NRCO—, —SO$_2$NR—, and —NRSO$_2$—, or terminated at the $R_f$ end with —CONR— or —SO$_2$NR— where $R_f$ is attached to the respective carbonyl carbon or sulfur atom thereof, and X is —S—, —O—, —SO$_2$, —NR—, —NRSO$_2$—, —SO$_2$NR—, —NRCO—, —CONR—, —C(R)$_2$—, —OOC—; or E is a direct bond and X is —CONR— or —SO$_2$NR— where $R_f$ is attached to the respective carbonyl carbon or sulfur atom thereof; R is defined as above; and $R_f$ is independently a straight or branched chain perfluoroalkyl of up to 18 carbon atoms or said perfluoroalkyl substituted by perfluoroalkoxy of 2 to 6 carbon atoms, or mixtures thereof.

2. A compound according to claim 1, wherein R' is alklyl of up to 4 carbon atoms.

3. A compound according to claim 2, wherein n is 1 to 100.

4. A compound according to claim 3, wherein $alk_1$ is alkylene of 3 to 10 carbon atoms; $alk_2$ and $alk_3$ are alkylene of 2 to 4 carbon atoms, or mixtures thereof, Z is hydrogen or lower alkyl, m is 1 to 50, E is alkylene of up to 3 carbon atoms, —CH$_2$CH$_2$S(C$_3$H$_5$OH)—, —CH$_2$CH$_2$SO$_2$(C$_3$H$_5$OH)— or —SO$_2$N(C$_2$H$_5$)CH$_2$CH$_2$S(CH$_2$)$_3$O(C$_3$H$_5$OH)—, X is —O—; $R_f$ is perfluoroalkyl of 4 to 12 carbon atoms or perfluoroalkyl of 2 to 6 carbon atoms substituted by perfluoroalkoxy of 2 to 6 carbon atoms, or mixtures thereof; and wherein group $C_3H_5OH$ refers to hydroxy substituted alkylene of 3 carbon atoms.

5. A compound according to claim 4 wherein m is 4 to 50 and the group $C_3H_5OH$ is —$CH_2CH(OH)CH_2$—, —$CH(CH_2OH)CH_2$— or —$CH_2CH(CH_2OH)$— or mixtures thereof.

6. A compound according to claim 1, of the formula

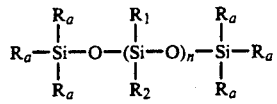

wherein $R_a$ is independently branched or straight chain alkyl of up to 18 carbon atoms, aryl of up to 10 carbon atoms or aralkylene of up to 14 carbon atoms; n is 1 to 200; at least one of $R_1$ and $R_2$ is $$-alk_1-O-(alk_2-O)_m-alk_3-X-E-R_f \quad (III)$$

and the remainder of $R_1$ and $R_2$ are independently branched or straight chain alkyl of up to 18 carbon atoms, aryl of up to 10 carbon atoms, aralkylene of up to 14 carbon atoms or $$-alk_1-O-(alk_2O)_m-alk_3-O-Z \quad (II)$$

wherein $alk_1$, $alk_2$, $alk_3$, X, E, $R_f$, m and Z are as in claim 1.

7. A compound according to claim 6, wherein $R_a$ is alkyl of 1 to 4 carbon atoms, n is 1 to 100, at least one of $R_1$ or $R_2$ is $$-alk_1-O-(alk_2-O)_m-alk_3-X-E-R_f$$

and the remainder of $R_1$ and $R_2$ are alkyl of 1 to 4 carbon atoms.

8. A compound according to claim 7 wherein $alk_1$ is alkylene of 3 to 10 carbon atoms; $alk_2$ and $alk_3$ are independently alkylene of 2 to 4 carbon atoms, or mixtures thereof, Z is hydrogen or lower alkyl; m is independently an integer from 1 to 50; E is alkylene of up to 3 carbon atoms, —$CH_2CH_2S(C_3H_5OH)$—, —$CH_2CH_2SO_2(C_3H_5OH)$— or —$SO_2N(C_2H_5)CH_2CH_2S(CH_2)_3O(C_3H_5OH)$—, and X is —O—; $R_f$ is perfluoroalkyl of 4 to 12 carbon atoms or perfluoroalkyl of 2 to 6 carbon atoms substituted by perfluoroalkoxy of 2 to 6 carbon atoms, or mixtures thereof.

9. The compound according to claim 1 of the formula

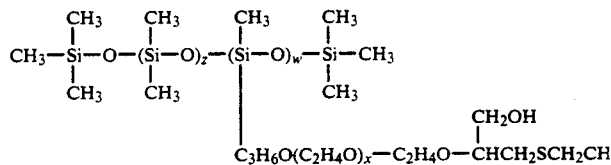

and its addition isomers:

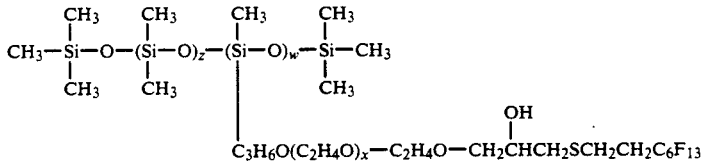

and

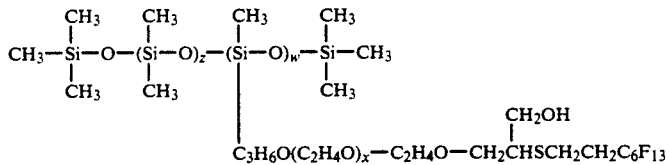

wherein $z \approx 5-20$, $w \approx 3-5$ and $x \approx 15-20$.

10. A compound according to claim 8, wherein Z is hydrogen or methyl.

11. A compound according to claim 8, wherein m is independently an integer from 4 to 50.

* * * * *